(12) United States Patent
Del Rio et al.

(10) Patent No.: US 7,621,730 B2
(45) Date of Patent: Nov. 24, 2009

(54) SURGICAL PNEUMATIC MOTOR

(75) Inventors: Eddy H. Del Rio, Royal Palm Beach, FL (US); Douglas A. Perry, Palm Beach Gardens, FL (US)

(73) Assignee: The Anspach Effort, Inc., Palm Beach Gardens, FL (US)

( * ) Notice: Subject to any disclaimer, the term of this patent is extended or adjusted under 35 U.S.C. 154(b) by 618 days.

(21) Appl. No.: 11/082,124

(22) Filed: Mar. 16, 2005

(65) Prior Publication Data

US 2005/0256512 A1 Nov. 17, 2005

Related U.S. Application Data

(60) Provisional application No. 60/567,188, filed on Apr. 30, 2004.

(51) Int. Cl.
*F01C 21/00* (2006.01)
*F03C 2/00* (2006.01)
*F04C 15/00* (2006.01)

(52) U.S. Cl. .................. 418/270; 418/82; 418/152; 418/178; 418/259; 418/268

(58) Field of Classification Search .............. 418/77, 418/78, 82, 107, 159, 266–270, 178, 259, 418/152

See application file for complete search history.

(56) References Cited

U.S. PATENT DOCUMENTS

| 2,159,232 | A | * | 5/1939 | Shaff | 418/82 |
| 3,453,936 | A | * | 7/1969 | Biek et al. | 418/82 |
| 3,700,363 | A | * | 10/1972 | Sorensen et al. | 418/270 |
| 3,832,088 | A | * | 8/1974 | Cromie | 415/199.5 |
| 4,599,058 | A | * | 7/1986 | Stone | 418/268 |

FOREIGN PATENT DOCUMENTS

JP 56056979 A * 5/1981 ............ 418/268

* cited by examiner

*Primary Examiner*—Theresa Trieu
(74) *Attorney, Agent, or Firm*—Norman Friedland (57) ABSTRACT

A modular constructed surgical motor with an outer cylindrical case used as the handle, and a spaced inner motor case resiliently mounted thereto forms an air gap for reducing vibrations and heat, a separate module houses the chuck, a ball coupling made from an elastomeric material transmits rotary motion, undercuts in the spindle adjacent the vanes and in the peripheral edge enhance power, the inlet opening to the vanes are positioned to increase the volume of inlet air, the inner surface of the cylinder is contoured to define a crescent seal, the inlet and outlet to the spindle are positioned in the cylinder to increase the power stroke, the discharge holes in the cylinder are oriented for uniform contact surface, the flow passages in the cylinder cool the cylinder and bearing, and one seal cured in situ and another seal adjacent the bearing prevent leakage of oil into ambient and the surgical tool.

48 Claims, 8 Drawing Sheets

PRIOR ART

FIG. 4D

PRIOR ART

SURGICAL PNEUMATIC MOTOR

This application claims the benefits under 35 U.S.C. § 119(e) of the U.S. provisional patent application 60/567,188 filed on Apr. 30, 2004.

CROSS REFERENCES

This invention relates to a the pneumatic motor that is designed be used in an MRI environment SURGICAL MOTOR USED WITH MRI, and is commonly assigned to The Anspach Effort, Inc. and was invented by myself and was filed as a provisional application 60/567,189 on Apr. 30, 2004 and is incorporated herein by reference.

FEDERALLY SPONSORED RESEARCH

None.

TECHNICAL FIELD

This invention relates to pneumatic motors for use by surgeons for performing surgical procedures that are typical in general surgery, neurosurgery, endoscopic, arthroscopic and the like and more particular to an improved pneumatic motor.

BACKGROUND OF THE INVENTION

To best understand this invention, it is helpful to know that the pneumatic motor of this invention is intended to replace three existing pneumatic surgical motors being manufactured and sold by the assignee and are well known in the medical industry as Black Max, Micro Max and Micro Max Plus and all of which are incorporated herein by reference. These prior art motors have been specifically developed for the medical industry and each in their own right have their own uniqueness. For example, the Black Max is a heavy duty motor that is more powerful and larger than the other two motors, but is heavier, hotter, noisier and vibrates more than these other motors. The Micro Max, supra, was developed to reduce the size, noise, vibration and heat and essentially be more gentle for use by the surgeon and likewise, has developed a niche in the industry. Obviously, the power is reduced. However, this motor for some medical procedures does not meet the needs of the surgeons because it lacked the necessary power which gave rise to the Micro Max Plus motor, which, again, has more power than the Micro Max but, yet, less power than the Black Max. The Micro Max Plus falls in the category of being more gentle for use by the surgeon but again, because of the increased power, heat, vibrations and weight of the Micro Max Plus (higher than the Micro Max but still lower than the Black Max) it, likewise, has gained a niche in the industry. A more technical way of looking at each of these motors is that the length of the cylinder supporting the vanes of the each of the motors are increased as a function of the power generated, namely, the lengths of the cylinders of the Black Max=1.0 inch ("), the Micro Max=¾" and the Micro Max Plus=½".

As one skilled in this technology will appreciate, the outside diameter of all of the well known commercially available pneumatic surgical motors including the ones noted in the above paragraphs are substantially equal and include a rotor that is driven by pressurized air for rotating a spindle that is rotatably supported by bearings in an outer housing that serves as the handle of the motor. All of these motors also include in some form or another the necessary seals, anti-rotational device, inlet and outlet for the pressurized air and means for lubricating the bearings and their support structures or internal housings.

We have found that we can provide an improved pneumatic surgical motor that satisfies the requirements of all the functions of the three motors that are discussed in the above paragraphs, but is an improvement there over while providing higher power with a smaller cylinder than the one in the Black Max, is lighter than the smallest of these motors, is cooler, exhibits less vibrations, is quieter and is as gentle to handle as is the smallest of these three motors. To differentiate the motor of the present invention from the pneumatic motors mentioned in the above paragraphs and the heretofore known motors it will be hereinafter referred to as the Xmax motor.

The following features of this invention discussed immediately below which are not to be construed as limitations thereto, contribute to the overall improvements to the inventive motor.

1. Smaller motor spherical ball bearing located at the fore end of the power cylinder provides a cavity within the housing to re-circulate the power cylinder's working compressed air which contributes to lowering the temperature of the bearing and affording improvements to the vibrations and heat characteristics.
2. Face seal disposed adjacent the inner race of the smaller bearing is deformed and cured in situ and enhances sealing of the air/lubricant mist in the motor housing, reduces heat generation and provides a sling action to the oil.
3. The vane on the spindle is designed to have increased vane working surface for augmenting the power of the motor.
4. Angled slots formed on the spindle to enhance the vanes ability to retract into the slot in opposition of centrifugal force so as to reduce friction and increase the life of the motor..
5. Exhaust holes formed in the cylinder discharging compressed air are judiciously located in columns to reduce wear and noise of the motor.
6. Cylinder input holes are oriented relative to the spindle vanes so as to increase input airflow acting on the vane's working surface.
7. The cylinder's inner surface adjacent to the outer surface of the spindle is off-set from round to define a crescent seal so as to increase the effectiveness of the spindle to cylinder gap seal and minimize lubrication requirements.
8. Slots in the cylinder formed adjacent to the inlet holes cool the cylinder before entering the vane motor.
9. A portion of the inlet air to the motor is diverted to flow to the front bearing and toward the aft end so as to air cool the front bearing housing and air cool the cylinder.
10. Provide cross over discharge holes to reduce noise by acoustical cancellation.
11. The motor housing is made from metallic material and may include an insert portion adjacent to where the surgeon will hold the motor an insert made from a heat resistant light weighted material so as to minimize the weight of the motor and afford comfort.
12. The modular construction of the motor includes an air gap between the outer surface of the motor housing and the insert motor housing which serves to provide cooling of the outer housing and isolates vibrations.
13. Modular construction where the insert motor housing is mounted on elastomeric mounts and utilizing the O-seal supporting the air inlet hose so as to reduce noise, temperature, vibration and facilitate assembly.
14. Coupling the motor to the output shaft with a resilient coupling to reduce vibration, noise, temperature and facilitate assembly.

15. Additional increased power is obtained by the orientation of the exhaust holes in the vane motor relative to the vane.
16. Isolation between motor and the lock shaft serves to assure that the axial loads generated by the cutter is isolated from the motor.

SUMMARY OF THE INVENTION

An object of this invention is to provide an improved surgical motor utilized in medical procedures.

The features of this surgical motor are enumerated in the above paragraphs and will be detailed hereinbelow.

In addition to the aforementioned features this invention includes an improved sealing that is formed in situ, inclusion of slots on the cylinder for cooling, suspension of the insert motor case, resilient coupling of the output shaft to the motor drive, isolation of the motor and lock shaft so that vibration of the cutter are not transmitted to the motor and the invention is characterized as providing additional power without sacrificing size, is cooler, has good feel characteristics to the user, requires minimal lubrication and has increased operating life. Because of the modular design of the motor, the chuck portion of the motor where the attachment and cutting tools are attached can be removed without having to dismantle the remaining portion of the motor. This facilitates the maintenance where heretofore the motor had to be disassembled in order to work on the chuck portion, which requires more maintenance than the motor portion.

The foregoing and other features of the present invention will become more apparent from the following description and accompanying drawings.

BRIEF DESCRIPTION OF THE DRAWINGS

These figures merely serve to further clarify and illustrate the present invention and are not intended to limit the scope thereof.

FIG. 4D1 is identical to FIG. 4D where the inner surface of the cylinder adjacent to the pinch point is undercut in accordance with this invention to define a crescent shaped seal;

FIG. 4E1 is a view identical to the view depicted in FIG. 4E where the inlet holes are relocated downstream of the pinch point to increase the volume of air being admitted to the vanes so enhance the power of the motor;

DETAILED DESCRIPTION OF THE INVENTION

While this invention is being shown in its preferred embodiment having elements that are designed to meet certain specifications to improve on the surgical drill, it will be appreciated that some elements may undergo changes and replacements as the instrument is being developed and these changes will be in the scope of this invention.

Figure 1:
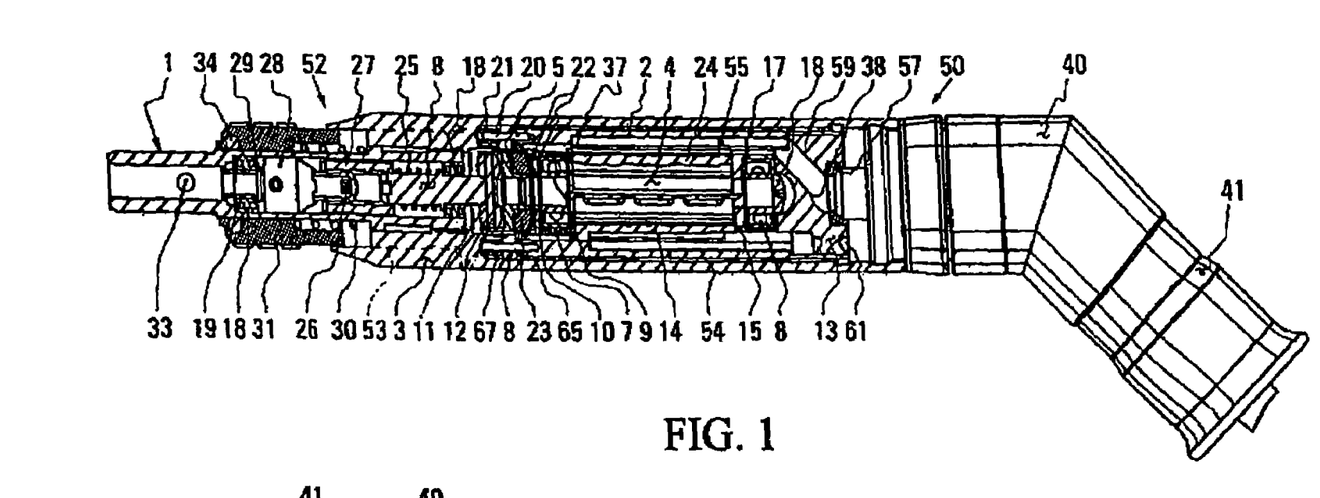
FIG. 1 is a longitudinal cut away sectional view showing the details of the motor of this invention and the chuck mechanism for attaching drill bits and various attachment assemblies.
Figure 2:
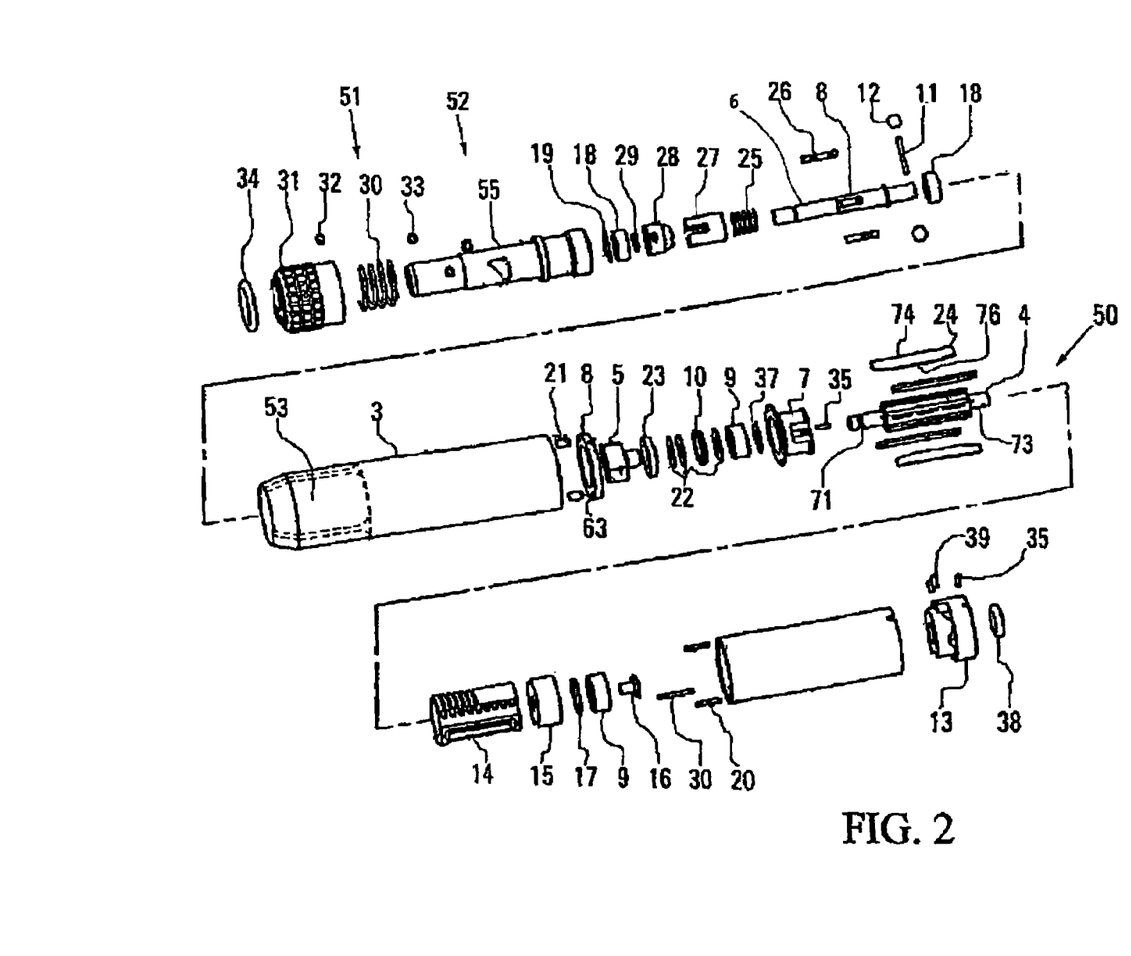
FIG. 2 is an exploded view illustrating the details of this invention.

The invention can best be understood by referring to FIGS. 1 and 2 showing the elements of the invention in an exploded view and then showing these same elements in the assembled condition comprising housing tube 1, insert or inner housing 2, motor or outer housing 3, spindle 4, coupling nut 5, pawl driven or output shaft (6), seal/bearing housing 7, isolation washer 8, bearing 9, support washer 10, drive pin 11, coupling ball 12, motor adapter 13, cylinder 14, back plate 15, machine screw 15, wave washer 17, bearing 18, wave washer 19, dowel pin 20, torque pin pad 21, seal 22 and 22a, seal retaining nut 23, vane 24, spring 25, pawls 26, lock cylinder 27, pawl release 28, snap ring 29, spring 30, sleeve disconnect 31, set screw 32, housing pin 33, O-ring 34, roll pin 35, pin 36, seal 37, O-ring 38, linear seal 39, swivel assembly 40 hose assembly 41 and set screw 42.

The surgical motor of this invention generally illustrated by reference numeral 51 includes essentially two major components, the motor or power generating module generally indicated by reference numeral 50 and the chuck portion module generally indicated by reference numeral 52. The chuck portion may include an attachment section which is well known and utilized in any number of surgical motors as referenced as prior art motors and a chuck that secures the tool bit. Unless any element is specifically referred to and described herein all other elements that are well known in the art for the sake of convenience and simplicity will not be described in this application. However, for more details reference should be made to the Black Max, Micro Max Plus and the Micro Max motors available from the assignee and all of which are incorporated herein by reference or to any other well known commercially available surgical motor. The elements that will not be described in detailed are primarily in the chuck module. Suffice it to say that the chuck serves to automatically attach the surgical tool (not shown) by virtue of the pawls 26 in the housing tube 1 and releases the same by virtue of the operator sliding the chuck sleeve 31 in a given direction to open the pawls so as to release the shaft of the surgical tool. In this design the sleeve 31 can rotate slightly to keep the pawls 26 of the chuck opened.

Figure 1A:
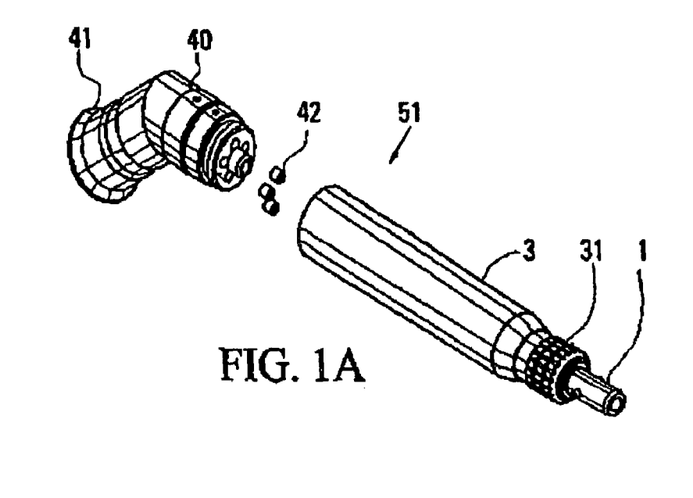
FIG. 1A is an exploded view in perspective illustrating in full the motor and chuck and the swivel attachment of this invention.

In accordance with this invention as best seem by FIGS. 1, 1A and 2, the surgical motor generally illustrated by reference numeral 51 is made in module construction by including a motor housing 3 and an insert motor housing 2. The motor housing 3 may include an outer sleeve 49 made from a plastic material mounted on the outer periphery of the fore end of housing 3 as shown in phantom as reference numeral 53 and may be included for the convenience of the surgeon. Without sleeve 53, the motor housing 3 is contoured in a cylindrical shape and tapered at the fore end, with the housing tube 1 extending therefrom as shown in FIG. 1A. The proximate end of the surgical tool fits into the housing tube 1 and the pawls 26 of chuck lock it in place. The pawls are extended when it is desired to remove the surgical tool. As noted from FIG. 2, in the assembled condition, the insert housing 2 is radially spaced from the motor housing (3) leaving an annular gap 54 that is filled with air. This air serves as an insulator to maintain a desirable heat and to absorb vibration to protect the outer surface of the motor housing 3 which is used as a handle for the surgeon when performing a surgical procedure.

Insert housing 2 is attached to the motor housing 3 by the dowel pins 8 that fit into the pair of drilled holes formed in both housings. The end of pins 8 fit into the torque pin pads 21 made from an elastomeric material which, in turn fit into drilled holes 65 formed in the housing 3. Obviously the torque pin pads 21 serves to isolate the insert motor from the motor housing 3 but also serves as an anti-rotation structure. The other end of the dowel pins 8 fit into the drilled holes formed at the end of the insert housing 2 to support the insert housing to the motor housing 3. The washer 8 fits between the insert housing 2 and the motor housing 3 and is made from an elastomeric material and the dowel pins 20 are inserted into the holes 63 and this subassembly is locked into place by nut 5. It is apparent from the foregoing that this subassembly serves to isolate the insert motor 2 from the motor housing 3 together with the O-seal 38 mounted in the motor adapter 13 located on the aft end of motor housing 3. The O-ring 36 mounted in the motor adapter 13 and the washer 8 serves to minimize vibrations and reduce noise. In addition the soft couple balls 12 made from an elastomeric material affords further protection against undesirable vibrations and hence, noise reduction.

Referring next to the power producing elements of the vane motor attention is drawn to FIGS. 1, 2, 3, 3A, 3B, 3C, 4, 4A, 4B, 4C, As will be described in more detail hereinbelow the vane motor generally illustrated by reference numeral 55 is sandwiched between the soft couple nut 5 and the motor adapter 15 and essentially includes a cylinder 14, spindle 4 and vanes 24 rotatably mounted in cylinder 14. The spindle includes stub shafts 61 and 63 extending from the fore and aft faces thereof and both shafts are supported by a pair of commercially available ball bearings 9. Because of the design characteristics of the vane motor, the ball bearings 9 are made smaller than what was required in heretofore design. The smaller bearings contribute to two features of the vane motor, 1) because they are smaller they create less noise and 2) the volume of the cavity adjacent the ball bearings 9 allows the ease of reversing the air flow of that portion of compressed air that passes over the cylinder and is returned into the cylinder as will be detailed hereinbelow. One edge of vanes 24 are crescent shape where the curved portion fits into the groove of the spindle and the other edge is flat which is exposed to the pressurized air as will be detailed in the description to follow.

This portion of the application will describe the cylinder 14 and spindle 4 and the details that serve to increase the power, reduce friction, decrease wear so as to enhance life of the motor and reduce noise of the vane motor without having to increase its size and for that matter reducing the size in comparison to other heretofore known motors. As can be seen in FIGS. 2, 4, 4A, 4B, and 4C each of the vanes 24 fit into the four off-set slots 58 formed in spindle and adjacent to these slots are a series of three axially extending spaced grooves 60 that extend radially inwardly toward the center axis of the spindle 4. The purpose of these grooves is to expose an additional working surface to the vane 24. As illustrated by the arrows A depicted in FIG. 4B the additional surface area increases the rotational force of the air acting on the vane. Additional working surface for increasing the force of the air acting on the spindle is by the incorporation of the axial slots 62. As seen by the arrow depicted in FIG. 4B the air impinges on the shoulder defined by the slot 62 to increase the force of air acting on the spindle. To reduce the friction of the vanes reciprocating into their respective slots, the slots 58 are displaced from the center line of the spindle 4. Because the vector line of action of the centrifugal force passes through the center line by virtue of this arrangement of these slots being off-set from the center line, the impact of the centrifugal force acting on the vanes as they rotate and retreat back into their respective slots is lessened and this in a sense lessens the drag of the vanes as they rotate around the periphery of the inner surface of the cylinder 14.

Figure 4:
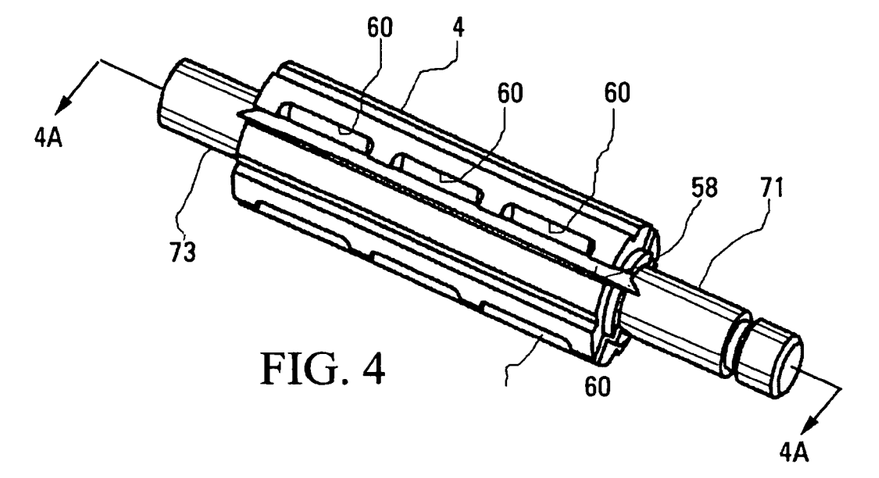
FIG. 4 is a perspective view of the spindle of the vane motor depicted in FIGS. 1 and 2.
Figure 4A:
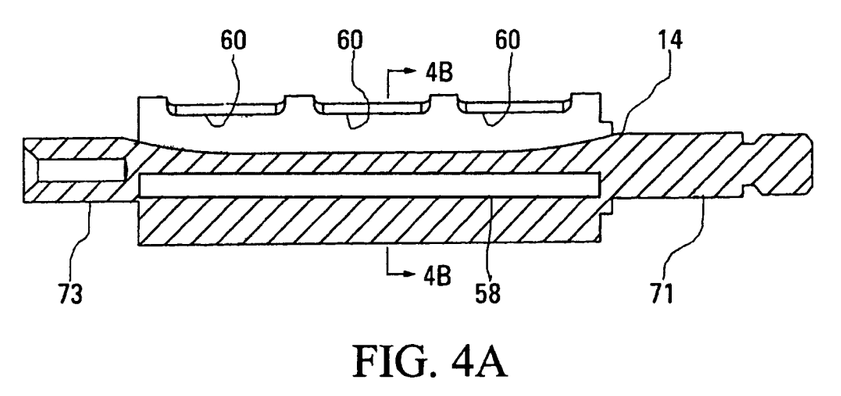
FIG. 4A is a sectional view taken along the longitudinal axis lines 4A-4A of the spindle depicted in FIG. 4.
Figure 4B:
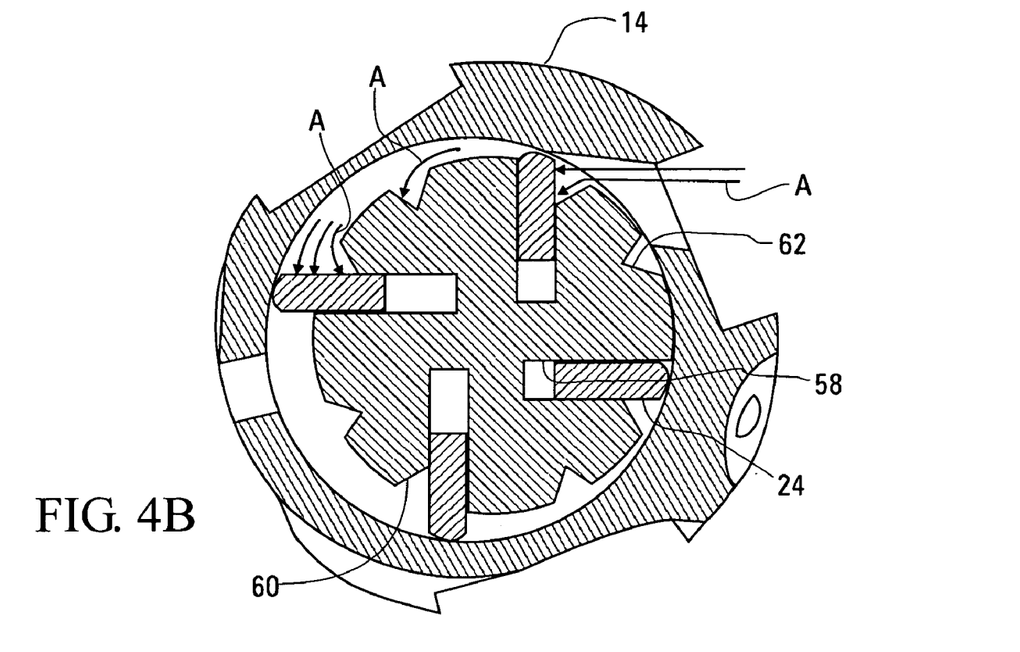
FIG. 4B is a view taken along the lateral axis 4B-4B showing the increased working area of the air flow acting on the vane and spindle depicted in FIG. 4.
Figure 4C:
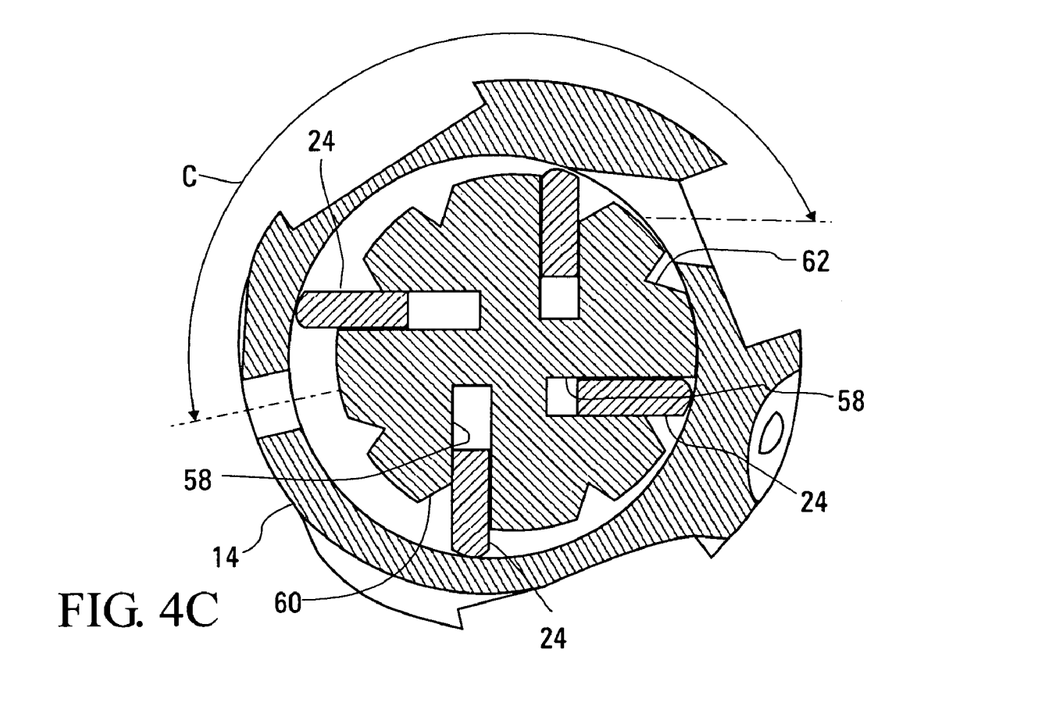
FIG. 4C is a view identical to the view depicted in FIG. 4B the distance between the cylinder inlet and the cylinder outlet illustrating the increased power stroke of the vane motor.
Figure 4D:
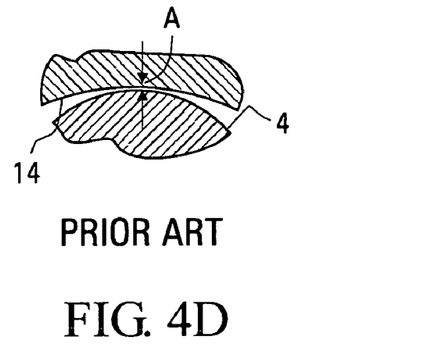
FIG. 4D is a schematic illustration of the relationship of the outer diameter of the spindle to the inner diameter of the cylinder showing a tangent point of contact (pinch point) in a prior art design.
Figures 4D, 4E:
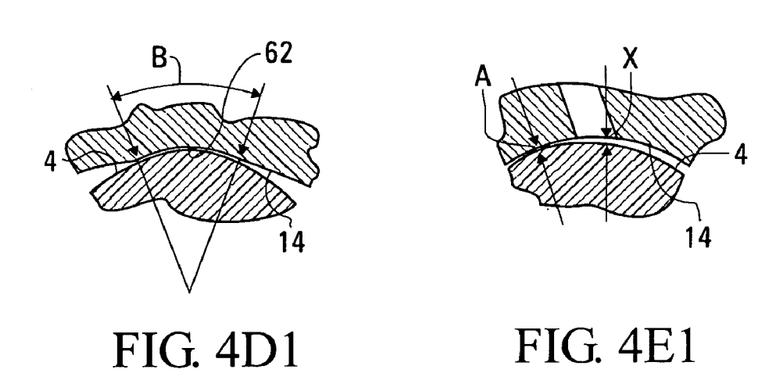
Figure 4E:
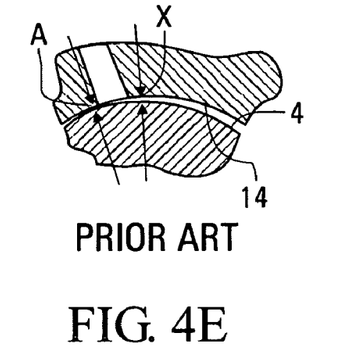
FIG. 4E is a view identical to the view in FIG. 4C illustrating the relationship of the inlet port of the cylinder to the vane of the spindle in a prior art configuration.

Likewise, the cylinder 14 of the vane motor and the spindle 4 are, changed from heretofore known vane motors by adding crescent seal as illustrated in FIGS. 4D and 4D'. As noted in FIG. 4D, because the spindle 4 is off-set from the center line of the cylinder 14 as is the case of heretofore known vane motors, the cylinder 14 comes closest to the inner diameter of the cylinder 14 at or close to the pinch point A. In this configuration the cylinder 14 is undercut at 62 and extend a circumferential distance indicated by line B. Obviously, the length of the gap is substantially increased so that the leakage path is increased which serves to reduce the leakage of pressurized air that is otherwise used to power the spindle 4. Further, the inlet air hole 70' in cylinder 14 is located to increase the volume of air immediately preceding the vane to further increase power. As noted in FIG. 4E the heretofore known vane motors always located the inlet air hole 70' to be at or close to the pinch point. In this embodiment the inlet hole 70" is located further downstream from the pinch point (lines x-x) that increases the volume defined by the space between the cylinder and spindle an hence allows more air to ingress adjacent to the vane.

As best seen in FIG. 4C there is a defined circumferential space between the inlet holes or apertures 70 and the air discharge hole or apertures 72. In heretofore known vane motors this distance was closer to each other than what is depicted in this FIG. 4C. By increasing this distance it was found that the power of the motor can be further increased.

According to this invention the increased space now becomes possible because the inlet hole 70 is displaced from the pinch point and the next adjacent vane passing the pinch point doesn't block the flow to the preceding vane allowing a larger expanse of travel of the vane in its power stroke.

Figure 6:
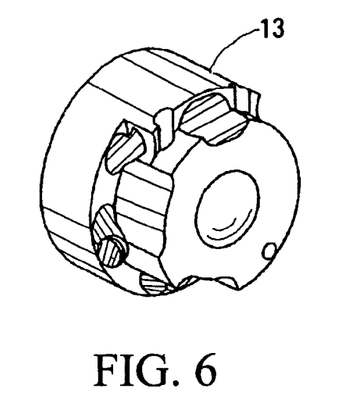
FIG. 6 is a perspective view of the motor adapter of the motor depicted in FIG. 1 illustrating the inlet air holes and the outlet cross over air holes of this invention.

In this Xmax motor the inlet air is admitted into a central opening 57 in the rear end of the motor and directed toward the outer periphery via the passageway 59 formed in the motor adapter 13. Passageway 59 is in communication the axial groove 76 formed in cylinder 14 to feed the inlet holes 70 while a portion flows over the fore bearings 9, over the bearing housing, and then back into the cylinder 14. Along the travel of the air toward the fore end a certain portion is admitted into the spindle while a portion serves to cool the cylinder 14 and the bearing 9 as described above. This is best illustrated in FIGS. 1, 3, 3A and 3B where air is admitted into the cylinder 14 via axial passageway 76 while a portion flows into inlet holes 70 via the axially spaced slots 78 formed in cylinder 14 downstream of the blockage portion 69 (outer diameter of cylinder 14) formed in cylinder 14 and the remaining portion leaves the cylinder to cool the bearings 9 before being re-admitted into the cylinder 14. The purpose of the blocking portion 69 and these slots 78 serve to cool the cylinder. As the air proceeds past the cylinder and forced to flow inwardly over the bearings toward the cylinder center line, the direction of the air then reverses to proceed toward the rear of the motor so that the remaining portion of the air is admitted into the spindle via axial slot 79 and holes 70 to act on the vanes and cause rotation thereof. Ultimately, all the pressurized inlet air feeds into the spindle to power the same via the vanes. The spent air exit the vane motor via the axial slot 81 and returned to the source of air via the motor adapter 13 (FIG. 6).

Because of the power enhancement from the features described above the diameter of the spindle shaft can be reduced allowing a smaller the bearing to support the spindle. This improved design made in accordance with this invention is creates an increased cavity surrounding the bearing housing which provide additional volume of air that flows out of the cylinder over the bearings and back into the cylinder enhancing the cooling capability of the motor vane. Obviously, this increased airflow serves to cool the bearings and hence, increase the life of the motor.

On the return to the outlet of the motor, the air flows through a plurality of judiciously oriented discharge holes 72. Not only is the circumferential distance between the inlet hole 70 and the exit hole 72 selected for increased power, the orientation of holes 72 are selected to avoid power losses and increase wear on the vane. Because of the arrangement of these holes in heretofore known surgical motors, there exhibited an unevenness of wear on the outer edge of the vanes. To avoid this unevenness as is illustrated in FIG. 3C.

Figures 3, 3A, 3B:
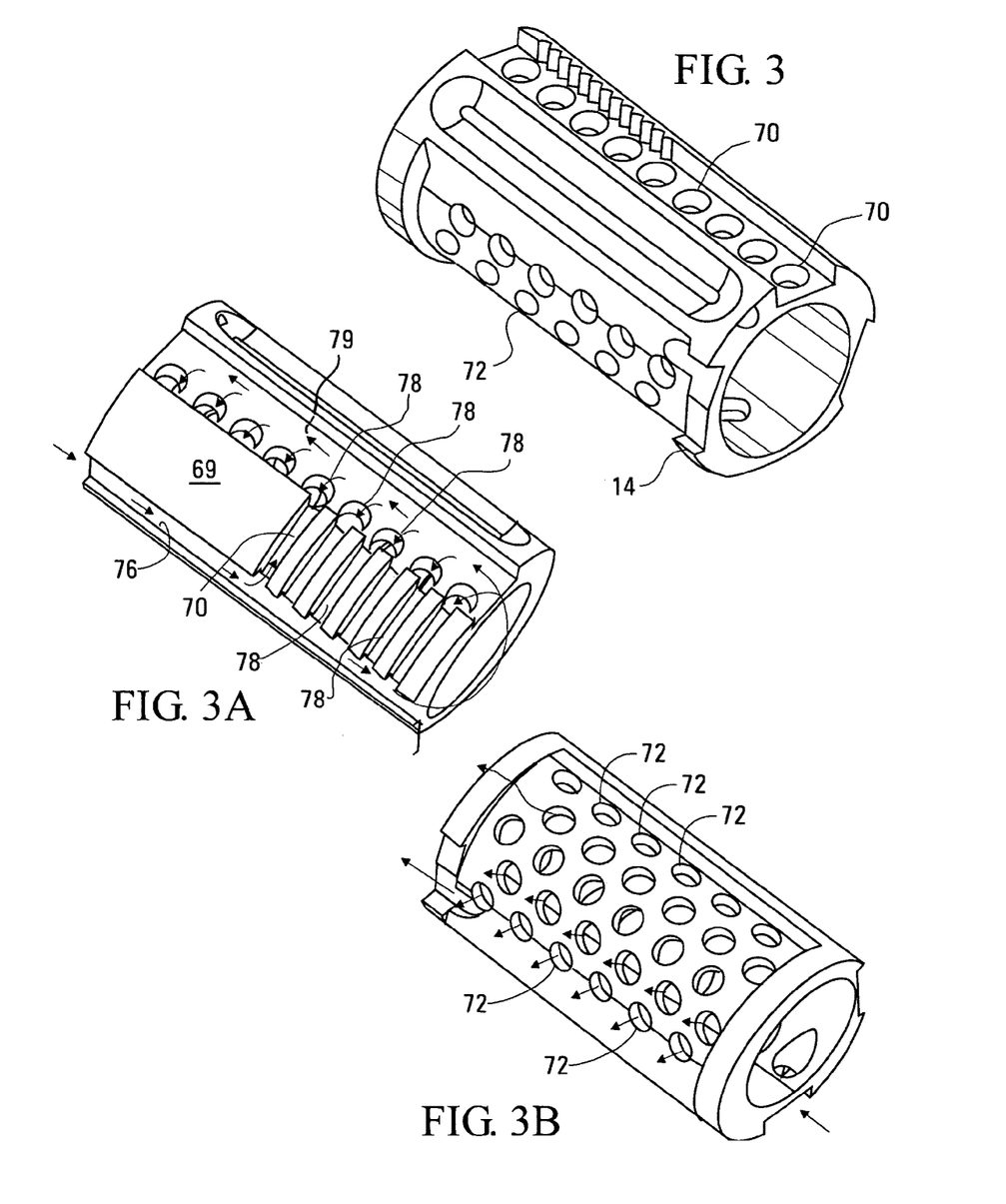
FIG. 3 is a perspective view of the cylinder of the vane motor of this invention.
FIG. 3A is an enlarged perspective view in elevation showing the details of the cooling slots of the cylinder depicted in FIG. 3.
FIG. 3B is an enlarged perspective view in elevation showing the details of the discharge slots of the cylinder depicted in FIG. 3.
Figure 3C:
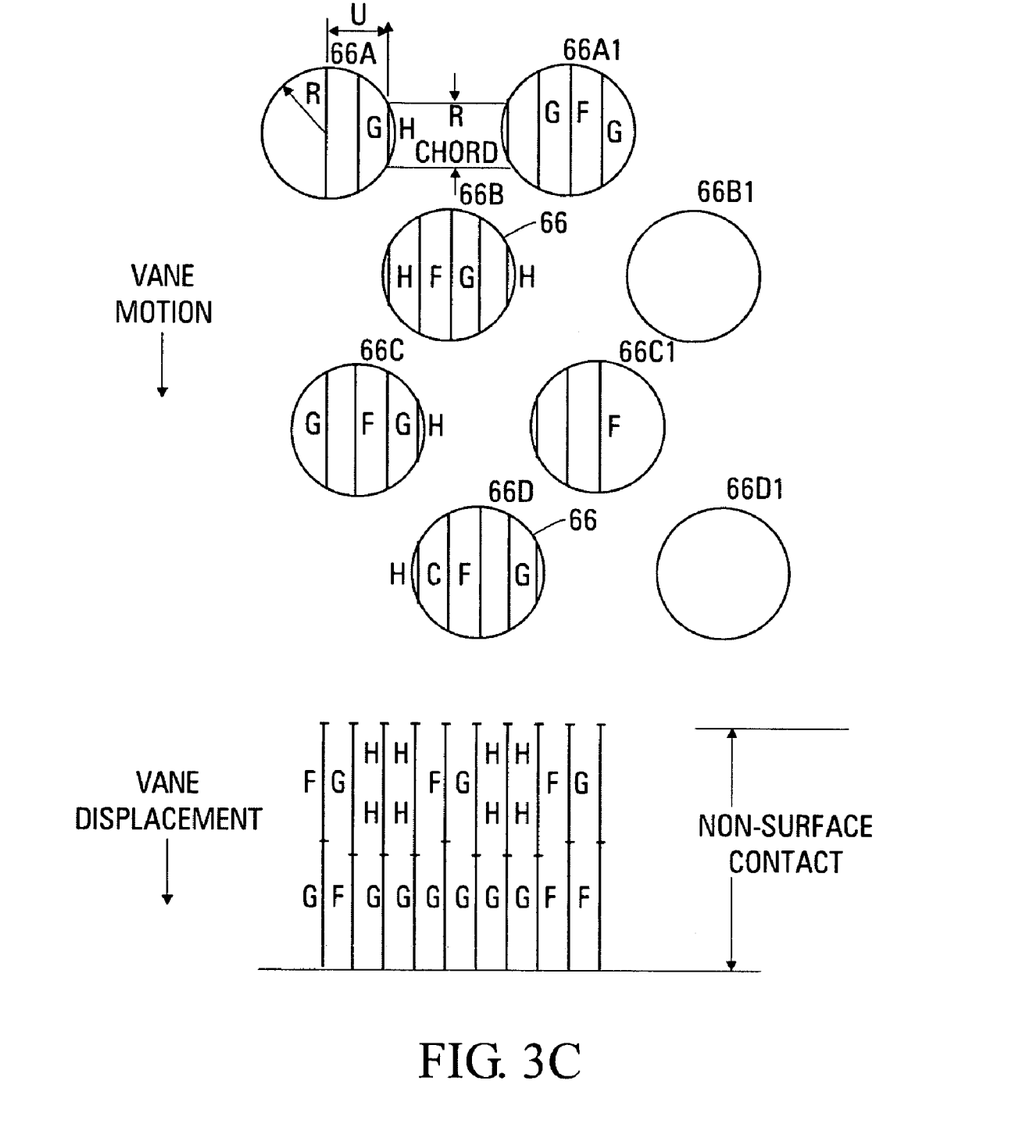
FIG. 3C is a schematic illustration of the orientation of the discharge holes formed in the cylinder depicted in FIG. 3 and a graph showing the vane displacement illustrating the surface/non-surface contact.

Attention is first directed to FIG. 3A which illustrates the discharge holes 72 judiciously disposed in cylinder 3 in a circumferential and axial direction and serve as the exhaust outlet for vane motor 55. These holes are arranged so that the vane passing thereunder will virtually see an even contact of the cylinder surface so as to eliminate the uneven wearing of the vane's outer edge. Because of the arrangement of the discharge ports in heretofore known surgical motors, there exhibited an unevenness of wear on the outer edge of the vanes. To avoid this unevenness as is illustrated in FIG. 3C the column of holes 72 identified as 72A, 72A1, 72B, 72B1, 72C, 72C1, 72D and 72D1, for each repeat in the pattern of holes the relative location of holes A and B is such that a unit of measure U is established for one hole and used to position all the other holes. Referring to hole 72A in FIG. 3C, the cord H at the right hand side is selected and it equals the radius R. The distance between the center line of hole 72A and this cord H establishes the unit U (the unit of measurement) which is used for the measurement to set the relative distance of all other cords within a column. Each space between cords (vertical lines) equals ½ the unit of measurement U. The spacing of rows is not critical save that the adjacent hole in a given row that does not overlap the adjacent hole. The hole 66B is established by aligning chords H of 72B with chords H of 72A and 72A1. The next row 72C is established by aligning the chord G with the centerline F of 72A. Row 72C1 is established by aligning centerline F of 72C1 with chord G of 72A1. With this pattern of holes, each of the vanes 2 will displace uniformly over the surface of the cylinder 3 as shown in FIG. 10. Referring to FIG. 10 showing one repeat of the hole pattern, it will be noted that the displacement of the first two chords over the holes 72A and 72C is equal to F and G. The next displacement over the holes 72A and 72C is equal to G and F. The next displacement of vane 2 is over the holes in 72A, 72B and 72C and this is equal to chords H, H and G. By following this pattern throughout the displacement of the vanes it will be noted that the total distance and hence, area that the edge of the vane is in contact with each of the holes of the cylinder is equal. It then follows that the total average area of contact that the edge of the vane relative to the surface of the cylinder is also equal. By designing the hole pattern of the cylinder in this manner, the vanes will wear evenly throughout its cycle and hence, will evidence a longer life.

According to this invention the inlet holes 70 and discharge holes 72 are formed as cylindrical holes which in heretofore known designs, these passages were other than cylindrical. Again, by contouring these holes in cylindrical form the power generated by the vane motor is increased.

Figure 5:
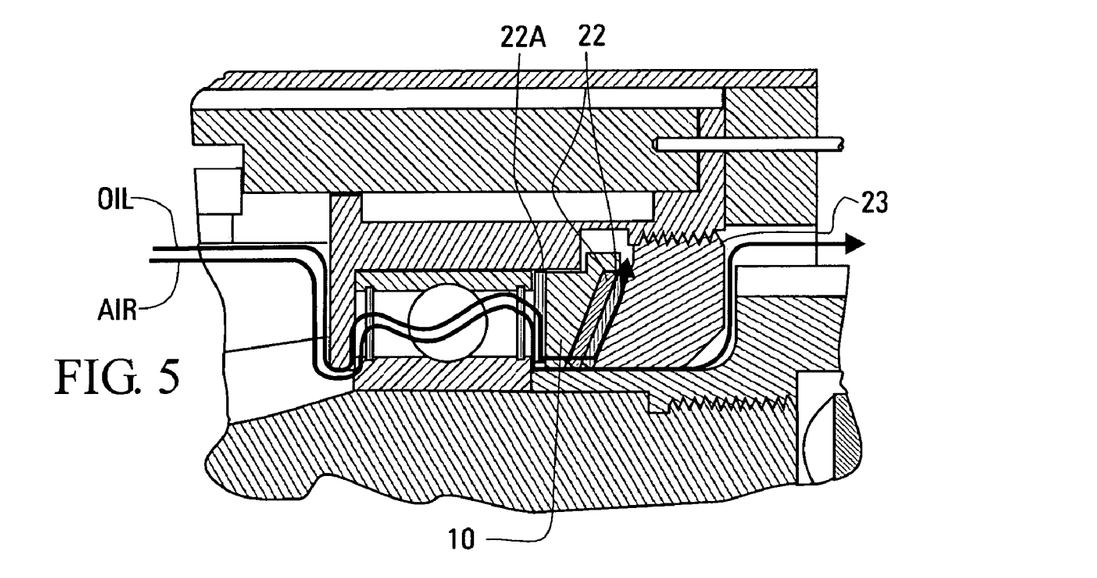
FIG. 5 is a schematic view illustrating the sealing arrangement for sealing the oil/air mist used in lubricating the vane motor depicted in FIGS. 1 and 2 so as to prevent oil leakage.

Both the front bearing and rear bearing for the spindle 4 are contained in a suitable bearing housing that is packed with grease and sealed to prevent the grease from escaping and for foreign matter to ingest therein. In this Xmax motor the air utilized to drive the vane motor carries a mist of lubrication. It is therefore important to provide proper sealing to assure adequate lubrication of the vanes and avoid oil from escaping to ambient. According to this invention and as can be seen from FIGS. 1 and 5, the dual seal 22 for the front bearing is formed in situ by configuring the seal retaining nut 23 and seal support washer 10 to support the pair of stationary seal 22 shaped in the form of discs. When mounted into the seal retaining nut 23 the shape of seal 22 is circular and is made with a close tolerance and is shaped much like a standard washer so when assembled it is tightly mounted into the housing and closely fitted to the shaft and the seals are forced between the seal washer and retainer and seek the angled position as shown. The edge of the seals are angled so that one edge bears against the rotating shaft . After assembly, the motor is rotated to its full power condition and the friction creating heat causes the seal which is made from a suitable plastic material such as Teflon® material to shrink the inner edges of the dual seal relative to the outer surface of the spindle shaft and defines a gap. This gap is sufficiently minuscule so that only air can migrate therethrough retaining the oil in the bearing compartment.

In addition, this dual seal works in conjunction with the single seal 22a (which is the same size, shape and material as the dual seal 22) which is axially spaced from the dual seal and supported by seal support washer 10 and being mounted adjacent to bearing 9 (at its left) and sandwiched and wedged in the bearing housing 7 in between the bearing 9 and the seal support washer 10 and extends radially from the inner face of the bearing housing 7 to adjacent the inner race 9a of bearing 9. Because of the fit of seal 22a which, like seal 22, is stationary, no leakage occurs at the inner face of the seal and bearing housing 7 and any leakage occurs adjacent to the inner race. This single seal 22a is important because the air/oil mist that comes in contact with the seal 22a at the inner race slings the oil in a direction toward the centerline of the spindle in the same as the direction of the centrifugal force and the air flows in the opposite direction. In other words, seal 22a serves to cause the flow of the oil mist to move toward the central axis of the spindle 4 and the air flows in a direction opposite to the centrifugal force generated by the spindle 4 rotating at approximately 80,000 RPM and flows in the direction toward the dual seal as depicted by the leakage path. As seen in FIG. 1, seal 37 mounted on the opposite side of this bearing 9 adjacent to the end of spindle 2 and is supported in the seal bearing housing 7. This seal 37 and the single seal 22 sandwich the front bearing 9 to assure that the oil is retained in the bearing compartment without leaking to ambient.

Figure 6A:
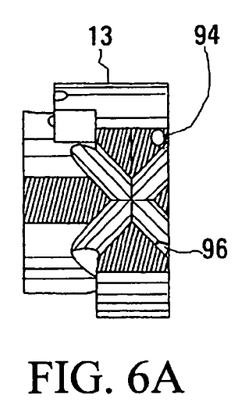
FIG. 6A is a sectional view taken along the longitudinal axis of the motor adapter depicted in FIG. 6.
Figure 6B:
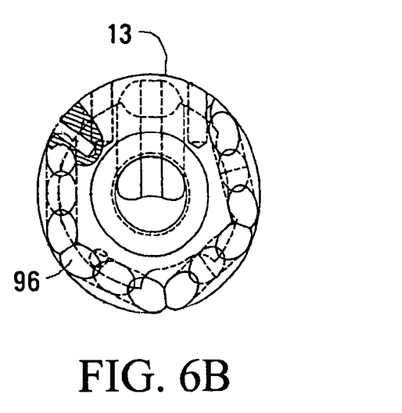
FIG. 6B is an end view of the motor adapter depicted in FIG. 6.
Figure 7:
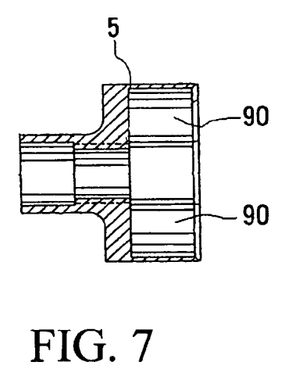
FIG. 7 is a sectional view of the soft couple nut depicted in FIG. 1.
Figure 7A:
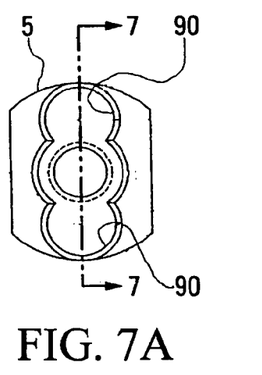
FIG. 7A is an end view of the soft couple nut depicted in FIG. 7.
Figure 8:
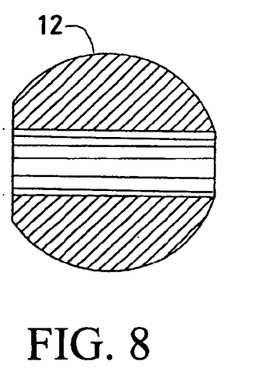
FIG. 8 is a plan view of the soft couple ball depicted in FIGS. 1 and 2.
Figure 9:
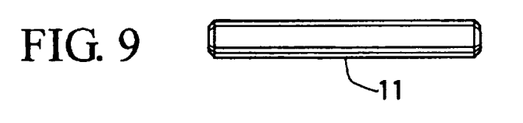
FIG. 9 is the cutter spindle drive pin depicted in FIGS. 1 and 2.

The next portion of this description describes the transmittal of power from the spindle to the output shaft of the Xmax motor. As seen in FIGS. 1, 2, 6, 6A, 6B, 7, and 7A spindle 4 is suitably threaded to the soft couple nut 5 and the motor adapter 13. Thus, the spindle drives the soft couple nut 5 and this rotary motion is transmitted to the output shaft 6 which in turn rotates the drill bit (not shown) that fits in the chuck assembly. To mitigate the vibrations that are generated by the vane motor. the drive connection from the spindle to the output shaft (i.e. the drive shaft to the driven shaft) is through the resilient balls or soft cutter balls 12 (FIGS. 1 and 8) made from a rubber material which is mounted on the cutter spindle drive pin 11 (FIG. 9). The balls fit into the recesses 90 formed at diametrically opposed ends in the soft couple nut 7 (FIG. 7). Rotary motion is transmitted to the the soft couple nut 5 is attached to the spindle through the balls 12 which, in turn, is pinned to shaft output shaft 6 via the pin 11 fitted through a laterally drilled hole in the shaft 6. Hence, the balls 12 serve to transmit the rotary motion to the output shaft 6 via the spindle 4 and soft couple nut 5.

In addition to the vibration absorbed through the ball drive 12 the insert motor housing 2 is soft mounted to the housing 3 via the torque pin pads 21 that surround the dowel pins 20 fitted into the complementary drilled holes formed in the housings 3 and 2. This together with the O-seal 38 mounted in motor adapter 13 sealing the air inlet from the hose and swivel assembly at the air inlet connection at the aft end of the motor serve to soft mount the motor and minimize vibratory motion felt in the outer surface of the housing 3 where the surgeon handles the drill.

To further reduce noise, the discharge air from the vane motor flows into the passages formed in the motor adapter 13. As can be seen in FIGS. 6 and 6A, motor adapter includes cross over holes 94 and 96, The design of these holes causes the discharge air to flow in a crisscross pattern and the air meeting and mixing dissipates a given amount of decibels resulting in a noise reductions.

Because the bearings supporting the chuck is isolated from the motor, the vibrations are not felt by the surgeon holding onto this assembly and because the output shaft is remote from and isolated from the bearings supporting the vane motor, the axial load generated by the drill bit or cutter is also not felt during a medical procedure. It will be appreciated that as the surgeon forces the cutting tool against the surface of the portion of the patient that is being operated on, this action develops a thrust load. This load passes through the cutter shaft (not shown) into the chuck module of the surgical motor and through the bearings 18 that shoulder against the motor housing 3, the thrust path then flows through the motor housing 3 where it is dissipated, bypassing the insert housing 2. Since the thrust loads do not pass through the vane motor, the vane motor only sees radial loads. This not only contributes to the efficacy of the surgical motor, it also allows the vane motor to be supported by smaller bearings as was noted in the above paragraph.

What has been shown by this invention is a new motor, designated for the sake of description the Xmax motor, that includes all the capabilities of providing high power and smooth performance with the ease of assembling the cutter and the attachments utilized in the medical procedures. In accomplishing these features, the Xmax motor is characterized as being more powerful, is quieter, vibration free and user friendly while increasing the life of the entire assembly and its component parts.

It is claimed:

1. A modular surgical motor (51) for powering surgical tools comprising a first module (52) supporting a vane motor (55) and a second module (50) supporting a chuck (28), said first module (52) including an outer housing (3) defining a handle for the surgeon, an insert housing (2) supported in said outer housing (3) and radially spaced therefrom defining with said outer housing an annular dead-ended space (54) adjacent to said handle and said space (54) being filled with air to dampen vibrations and to insulate said handle from heat, said insert housing (2) includes a motor adapter (13) disposed on the aft end of said insert housing (2) for enclosing the end thereof, a center bore (57) formed therein for receiving pressurized air, a passageway (59) in said motor adapter (13) in fluid communication with said center bore (57) for leading the pressurized air toward the outer periphery of said insert housing (2) and another bore (61) formed in the peripheral portion of said motor adapter for leading discharge air out of said insert motor.

2. A modular surgical motor (51) as claimed in claim 1 including an O-seal (38) mounted in said bore (57), a pair of dowel pins (20), a washer made (8) from an elastomeric material mounted on the fore end of said insert housing (2) and having a pair of apertures (63), said dowel pins (20) disposed in coincidence with aligned drilled holes (65,67) formed in said insert housing (2) and in said outer housing (3) and in said pair of apertures (63) for supporting said washer (8), said washer (8) and said O-ring (38) providing the support for said insert housing (2) whereby said insert housing (2) is isolated from said outer housing (3).

3. A modular surgical motor (51) as claimed in claim 2 including an output shaft (6) mounted in said second module (50) for rotary supporting the surgical tools, ball bearings (18) rotary supporting said output shaft (6), the surgical tools when in operation imparting thrust loads to said output shaft (6), said ball bearings (18) transmitting said thrust loads to said outer housing (3) and bypassing said insert housing (2) wherein said vane motor (55) is isolated from said thrust loads.

4. A modular surgical motor (51) as claimed in claim 3 including an interconnection (5) from said vane motor (55) to said output shaft (6), said interconnection (5) including balls (12) made from elastomeric material for transmitting rotary motion from said vane motor (55) to said output shaft (6) whereby vibrations created by said vane motor (55) are absorbed by said balls (12).

5. A modular surgical motor (51) as claimed in claim 4 wherein said vane motor (55) includes a cylinder (14), a spindle (4) rotary mounted in said cylinder (3), and circumferentially spaced vanes (24) disposed in slots (58) formed in said cylinder (14), said spindle (4) having opposing stub shafts (71,73) extending on the fore side and aft side of said spindle (4) and being in coincidence with the center of said insert housing (2), at least one ball bearing (9) mounted on said stub shaft (71) located on the fore side of said spindle (4), whereby said O-seal (38), said washer (8), said ball bearing (9) and said annular gap (54) attenuate the noise generated by said vane motor (55).

6. A modular surgical motor (51) as claimed in claim 5 including a pair of cylindrical torque pin pads (21) made from elastomeric material mounted in the drilled holes (65) of said upper housing (3) and each of said pair of cylindrical torque pin pads (21) having a central aperture for receiving said dowel pins (20) whereby said torque pin pads (21) enhance noise reduction of said vane motor (55).

7. 6A modular surgical motor (51) as claimed in claim 6 wherein each of said vanes (24) includes an upper edge (74) being straight and a lower edge (75) being contoured and disposed in each of said slots (58), and said slots (58) being eccentrically disposed relative to the center on said spindle (4).

8. A modular surgical motor (51) as claimed in claim 7 wherein said vanes (24) includes a power face where the pressurized air impinges for powering said spindle (4), said spindle (4) having an axial undercut (60) formed on the periphery thereof adjacent to said vanes (24) for increasing the power lace of said vanes (24) for enhancing the power of said spindle (4).

9. A modular surgical motor (51) as claimed in claim 8 wherein said spindle (4) includes at least one slot (62) formed on the periphery of said spindle (4) and spaced between adjacent vanes (24) and having a power face where pressurized air impinges for enhancing the power of said spindle (4).

10. A modular surgical motor (51) as claimed in claim 6 wherein said cylinder (14) is eccentrically spaced relative to said spindle (4), said cylinder including a plurality of axially spaced inlet apertures (70) for receiving pressurized air for powering said spindle (4), an axial passageway (76) formed in said cylinder (14) for flowing pressurized air to said inlet apertures, a first portion on the aft end of said cylinder 14 blocking the flow of pressurized air from said inlet apertures (70), a plurality of axially spaced grooves (78) formed in the fore end of said cylinder (14) interconnecting said axial passageway (76) with said inlet apertures (70) whereby said grooves (78) cool said cylinder (14).

11. A modular surgical motor (51) as claimed in claim 10 wherein a portion of said pressurized air flows past the fore end of said cylinder (14) and reverses and flows toward the aft end of said cylinder 14 and into the inlet apertures (70) of said cylinder (14).

12. A modular surgical motor (51) as claimed in claim 11 wherein said cylinder includes a plurality of circumferential and axially spaced discharge holes (72) wherein said cylinder includes a row of axially spaced inlet apertures, an axial slot formed adjacent to said apertures for leading pressurized air into the cylinder, and said discharge holes are cylindrically shaped.

13. A modular surgical motor (51) as claimed in claim 12 wherein the inlet apertures (70) are cylindrical in shape.

14. A modular surgical motor (51) as claimed in claim 13 wherein said discharge apertures (72) are prearranged in a given pattern of columns and rows, each row of apertures (72) do not overlap the next adjacent row of apertures, the straight edge (73) of vanes (24) as it travels over the columns of apertures (72) are arranged to provide a constant surface contact with the surface of said cylinder (14) during each revolution of travel creating uniform wear of said straight edge (73) enhancing the life of said vane motor (55).

15. A modular surgical motor (51) as claimed in claim 13 including a disc shaped first seal (22a) mounted in the seal housing (7) and wedged between the seal support washer rigidly supported in a fixed position in insert housing (2) and ball bearing (9), said ball bearing (9) having an inner race (9a), said seal (22a) extending from the seal support housing to said inner race (9a) and defining a minuscule gap for permitting a minuscule amount of air/oil mist to escape and causing the oil to flow toward the center of said spindle (4).

16. A modular surgical motor (51) as claimed in claim 13 including seal (22) shaped in the form of a disc mounted adjacent the spindle stub shaft (61) to prevent leakage of oil from said bearing (9), seal support washer (10) and seal retaining nut (23) mounted in said insert housing, seal (22) wedged between said seal support washer (10) and said seal retaining nut (23) and adjacent said stub shaft (61), said seal (22) being made from a thermal setting material and being made operable in situ by rotating said stub shaft (61) of said vane motor to generate sufficient friction and heat to cause said seal (22) to deform in the shape of the contour of the face of seal retaining nut (23) and become operable wherein the edge of said seal (22) deforms to define a minuscule gap between said seal (22) and stub shaft (61) to prevent oil from leaking while allowing air to leak.

17. A modular surgical motor (51) as claimed in claim 15 including seal (22) axially spaced from seal (22a), said seal (22) being shaped in the form of a disc mounted adjacent the spindle stub shaft (61) to prevent leakage of oil from said bearing (9), seal support washer (10) and seal retaining nut (23) mounted in said insert housing, seal (22) wedged between said seal support washer (10) and said seal retaining nut (23) and adjacent said stub shaft (61), said seal (22) being made from a thermal setting material and being made operable in situ by rotating said stub shaft (61) of said vane motor to generate sufficient friction and heat to cause said seal (22) to deform in the shape of the contour of the face of seal retaining nut (23) and become operable wherein the edge of said seal (22) deforms to define a minuscule gap between said seal (22) and stub shaft (61) to prevent oil from leaking while allowing air to leak whereby the seal (22) and first seal (22a) prevent oil from escaping into the surgical tools being controlled by said surgical motor (51).

18. A surgical motor (51) for powering surgical tools having a motor housing (3) defining a handle for the surgeon to grasp, an insert housing (2) radially spaced inwardly from said motor housing (3) and defining therewith an elongated annular gap ((54) for capturing air, a vane motor (55) disposed in said insert housing (2) having a non-rotating cylinder (14) and a rotating spindle (4) mounted in said cylinder, said spindle having a plurality of circumferentially spaced vanes (24) mounted for reciprocal movement in slots formed in said cylinder, said rotating spindle (4) and said cylinder (14) being eccentrically mounted relative to each other so that the vane (24) comes in contact with the surface of said cylinder (14) during the power stroke of the vane (24), an input shaft attached to said spindle (4) and driven thereby and an output shaft (6) for supporting the surgical tools powered by said surgical motor (51), means for coupling said input shaft (61) to said output shaft (6) including a pair of diametrically opposed balls (12) made from elastomeric material whereby the vibrations of said vane motor are attenuated 19. A surgical motor as claimed in claim 18 wherein said means for coupling include a drive pin (11) extending laterally from said input shaft (61) and fitted into a aperture formed therein, a coupling nut 5 attached to said input shaft (61) and having pockets contoured to support said balls (12)

whereby the rotary motion from said spindle (4) is transferred to said output shaft (6) via the balls 12 for reducing vibration and noise.

20. A surgical motor (51) as claimed in claim 19 wherein said insert housing (2) includes a motor adapter (13) disposed on the aft end of said insert housing (2) for enclosing the end thereof, a center bore (57) formed therein for receiving pressurized air, a passageway (59) in said motor adapter (13) in fluid communication with said center bore (57) for leading the pressurized air toward the outer periphery of said insert housing (2) and another bore (61) formed in the peripheral portion of said motor adapter for leading discharge air out of said insert motor.

21. A surgical motor (51) as claimed in claim 20 including an O-seal (38) mounted in said bore (57), a pair of dowel pins (20), a washer made (8) from an elastomeric material mounted on the fore end of said insert housing (2) and having a pair of apertures (63), said dowel pins (20) disposed in coincidence with aligned drilled holes (65,67) formed in said insert housing (2) and in said outer housing (3) and in said pair of apertures (63) for supporting said washer (8), said washer (8) and said O-ring (38) providing the support for said insert housing (2) whereby said insert housing (2) is isolated from said outer housing (3).

22. A surgical motor (51) as claimed in claim 21 including an output shaft (6) mounted in said second module (50) for rotary supporting the surgical tools, ball bearings (18) rotary supporting said output shaft (6), the surgical tools when in operation imparting thrust loads to said output shaft (6), said ball bearings (18) transmitting said thrust loads to said outer housing (3) and bypassing said insert housing (2) wherein said vane motor (55) is isolated from said thrust loads.

23. A surgical motor (51) as claimed in claim 22 wherein said vane motor (55) includes a cylinder (14), a spindle (4) rotary mounted in said cylinder (14), and circumferentially spaced vanes (24) disposed in slots (58) formed in said cylinder (14), said spindle (4) having opposing stub shafts (71, 73) extending on the fore side and aft side of said spindle (4) and being in coincidence with the center of said insert housing (2), at least one ball bearing (9) mounted on said stub shaft (71) located on the fore side of said spindle (4), whereby said O-seal (38), said washer (8), said ball bearing (9) and said annular gap (54) attenuate the noise generated by said vane motor (55).

24. A surgical motor (51) as claimed in claim 23 including a pair of cylindrical torque pin pads (21) made from elastomeric material mounted in the drilled holes (65) of said upper housing (3) and each of said pair of cylindrical torque pin pads (21) having a central aperture for receiving said dowel pins (20) whereby said torque pin pads (21) enhance noise reduction of said vane motor (55).

25. A surgical motor (51) as claimed in claim 24 wherein each of said vanes (24) includes an upper edge (74) being straight and a lower edge (75) being contoured and disposed in each of said slots (58), and said slots (58) being eccentrically disposed relative to the center on said spindle (4).

26. A surgical motor (51) as claimed in claim 25 wherein said vanes (24) includes a power face where the pressurized air impinges for powering said spindle (4). said spindle (4) having an axial undercut (60) formed on the periphery thereof adjacent to said vanes (24) for increasing the power face of said vanes (24) for enhancing the power of said spindle (4).

27. A surgical motor (51) as claimed in claim 26 wherein said spindle (4) includes at least one slot (62) formed on the periphery of said spindle (4) and spaced between adjacent vanes (24) and having a power face where pressurized air impinges for enhancing the power of said spindle (4).

28. A surgical motor (51) as claimed in claim 25 wherein said cylinder (14) is eccentrically spaced relative to said spindle (4), said cylinder including a plurality of axially spaced inlet apertures (70) for receiving pressurized air for powering said spindle (4), an axial passageway (76) formed in said cylinder (14) for flowing pressurized air to said inlet apertures, a first portion on the aft end of said cylinder (14) blocking the flow of pressurized air from said inlet apertures (70), a plurality of axially spaced grooves (78) formed in the fore end of said cylinder (14) interconnecting said axial passageway (76) with said inlet apertures (70) whereby said grooves (78) cool said cylinder (14).

29. A surgical motor (51) as claimed in claim 28 wherein a portion of said pressurized air flows past the fore end of said cylinder (14) and reverses and flows toward the aft end of said cylinder (14) and into the inlet apertures (70) of said cylinder (14), an axial slot formed adjacent to said apertures for leading said portion of pressurized air into the cylinder (14).

30. A surgical motor (51) as claimed in claim 29 wherein said cylinder includes a plurality of circumferential and axially spaced discharge cylindrical holes (72) and said discharge holes being cylindrically shaped.

31. A modular surgical motor (51) as claimed in claim 30 wherein the inlet apertures (70) are cylindrical in shape.

32. A surgical motor (51) as claimed in claim 31 wherein said discharge apertures (72) are prearranged in a given pattern of columns and rows, each row of apertures (72) do not overlap the next adjacent row of apertures, the straight edge (73) of vanes (24) as it travels over the columns of apertures (72) are arranged to provide a constant surface contact with the surface of said cylinder (14) during each revolution of travel creating uniform wear of said straight edge (73) enhancing the life of said vane motor (55).

33. A surgical motor (51) as claimed in claim 32 including a disc shaped first seal (22a) mounted in the seal housing (7) and wedged between the seal support washer rigidly supported in a fixed position in insert housing (2) and ball bearing (9), said ball bearing (9) having an inner race (9a), said seal (22a) extending from the seal support housing to said inner race (9a) and defining a minuscule gap for permitting a minuscule amount of air mist to escape and causing the oil to flow toward the center of said spindle (4).

34. A surgical motor (51) as claimed in claim 33 including seal (22) shaped in the form of a disc mounted adjacent the spindle stub shaft (61) to prevent leakage of oil from said bearing (9), seal support washer (10) and seal retaining nut (23) mounted in said insert housing, seal (22) wedged between said seal support washer (10) and said seal retaining nut (23) and adjacent said stub shaft (61), said seal (22) being made from a thermal setting material and being made operable in situ by rotating said stub shaft 61 of said vane motor to generate sufficient friction and heat to cause said seal (22) to deform in the shape of the contour of the face of seal retaining nut (23) and become operable wherein the edge of said seal (22) deforms to define a minuscule gap between said seal (22) and stub shaft (61) to prevent oil from leaking while allowing air to leak.

35. A surgical motor (51) as claimed in claim 34 including seal (22) axially spaced from seal (22a), said seal (22) being shaped in the form of a disc mounted adjacent the spindle stub shaft (61) to prevent leakage of oil from said bearing (9), seal support washer (10) and seal retaining nut (23) mourned in said insert housing, seal (22) wedged between said seal support washer (10) and said seal retaining nut (23) and adjacent said stub shaft (61), said seal (22) being made from a thermal setting material and being made operable in situ by rotating said stub shaft (61) of said vane motor to generate sufficient friction and heat to cause said seal (22) to deform in the shape of the contour of the face of seal retaining nut (23) and become operable wherein the edge of said seal (22) deforms to define a minuscule gap between said seal (22) and stub shaft (61) to prevent oil from leaking while allowing air to leak whereby the seal (22) and first seal (22a) prevent oil from escaping into the surgical tools being controlled by said surgical motor (51).

36. A modular surgical motor (51) for powering surgical tools comprising a first module (52) supporting a vane motor (53) and a second module (50) supporting a chuck (28), said first module (52) including an outer housing (3) defining a handle for the surgeon, an insert housing (2) supported in said outer housing (3) and radially spaced therefrom defining with said outer housing an annular space (54) and said space (54) being filled with air to dampen vibrations and to insulate said handle from heat, said insert housing (2) including a motor adapter (13) disposed on the aft end of said insert housing (2) for enclosing the end thereof, a center bore (57) formed therein for receiving pressurized air, a passageway (59) in said motor adapter (13) in fluid communication with said center bore (57) for leading the pressurized air toward the outer periphery of said insert housing (2) and another bore (61) formed in the peripheral portion of said motor adapter for leading discharge air out of said insert motor, said vane motor (55) includes a cylinder (14), a spindle (4) rotary mounted in said cylinder (3), and circumferentially spaced vanes (24) disposed in slots (58) formed in said cylinder (14), said spindle (4) having opposing stub shafts (71,73) extending on the fore side and aft side of said spindle (4) and being in coincidence with the center of said insert housing (2), said vanes (24) includes a power face where the pressurized air impinges for powering said spindle (4), said spindle (4) having an axial undercut (60) formed on the periphery thereof adjacent to said vanes (24) for increasing the power face of said vanes (24) for enhancing the power of said spindle (4), said spindle (4) includes circumferentially spaced slots (62) formed on the periphery of said spindle (4) and spaced between adjacent vanes (24) and having a power face where pressurized air impinges for enhancing the power of said spindle (4), said cylinder (14) is eccentrically spaced relative to said spindle (4), said cylinder including a plurality of axially spaced inlet cylindrical holes (70) for receiving pressurized air for impinging on said vanes for powering said spindle (4), an axial passageway (76) formed in said cylinder (14) for flowing pressurized air to said inlet cylindrical holes in fluid communication with said passageway (59), a first portion on the aft end of said cylinder (14) blocking the flow of pressurized air from said inlet cylindrical holes (70), a plurality of axially spaced grooves (78) formed in the fore end of said cylinder (14) interconnecting said axial passageway (76) with said inlet apertures (70), a portion of said pressurized air flows past the fore end of said cylinder 14 and reverses and flows toward the aft end of said cylinder 14 and into the inlet cylindrical holes (70) of said cylinder (14), said cylinder includes a plurality of circumferential and axially spaced discharge holes (72) in fluid communication with said center bore (57), and ball bearing (9), said ball bearing (9) having an inner race (9a), said seal (22a) extending from the seal support housing to said inner race (9a) and defining a minuscule gap for permitting a minuscule amount of air/oil mist to escape and causing the oil to flow toward the center of said spindle (4), a seal (22) shaped in the form of a disc mourned adjacent to the spindle stub shaft (61) to prevent leakage of oil from said bearing (9), seal support washer (10) and seal retaining nut (23) mounted in said insert housing, seal (22) wedged between said seal support washer (10) and said seal retaining nut (23) and adjacent said stub shaft (61), said seal (22) being made from a thermal setting material and being made operable in situ by rotating said stub shaft 61 of said vane motor to generate sufficient friction and heat to cause said seal (22) to deform in the shape of the contour of the face of seal retaining nut (23) and become operable wherein the edge of said seal (22) deforms to define a minuscule gap between said seal (22) and stub shaft (61) to prevent oil from leaking while allowing air to leak.

37. A surgical motor (51) for powering surgical tools having a motor housing (3) defining a handle for the surgeon to grasp, an insert housing mounted in said motor housing, a vane motor (55) disposed in said insert housing (2) having a non-rotating cylinder (14) and a rotating spindle (4) mounted in said cylinder, said spindle having a plurality of circumferentially spaced vanes (24) mourned for reciprocal movement in slots formed in said cylinder, said rotating spindle (4) and said cylinder (14) being eccentrically mounted relative to each other so that the vane (24) comes in contact with the surface of said cylinder (14) during the power stroke of the vane (24), an input shaft attached to said spindle (4) and driven thereby and an output shaft (6) for supporting the surgical tools powered by said surgical motor (51), means for coupling said input shaft (61) to said output shaft (6), said insert housing (2) includes a motor adapter (13) disposed on the aft end of said insert housing (2) for enclosing the end thereof, a center bore (57) formed therein for receiving pressurized air, a passageway (59) in said motor adapter (13) in fluid communication with said center bore (57) for leading the pressurized air toward the outer periphery of said insert housing (2) and another bore (61) formed in the peripheral portion of said motor adapter for leading discharge air out of said insert motor.

38. A surgical motor (51) as claimed in claim 37 wherein each of said vanes (24) includes an upper edge (74) being straight and a lower edge (75) being contoured and disposed in each of said slots (58), and said slots (58) being eccentrically disposed relative to the center on said spindle (4).

39. A surgical motor (51) as claimed in claim 38 wherein said vanes (24) includes a power face where the pressurized air impinges for powering said spindle (4). said spindle (4) having an axial undercut (60) formed on the periphery thereof adjacent to said vanes (24) for increasing the power face of said vanes (24) for enhancing the power of said spindle (4).

40. A surgical motor (51) as claimed in claim 39 wherein said spindle (4) includes at least one slot (62) formed on the periphery of said spindle (4) and spaced between adjacent vanes (24) and having a power face where pressurized air impinges for enhancing the power of said spindle (4).

41. A surgical motor (51) as claimed in claim 40 wherein said cylinder includes a plurality of axially spaced inlet apertures (70) for powering said spindle (4), an axial passageway (76) formed in said cylinder (14) for flowing pressurized air from said passageway (59) to said inlet apertures, a first portion on the aft end of said cylinder (14) blocking the flow of pressurized air from said inlet apertures (70), a plurality of axially spaced grooves (78) formed in the fore end of said cylinder (14) interconnecting said axial passageway (76) with said inlet apertures (70) whereby said grooves (78) cool said cylinder (14).

42. A surgical motor (51) as claimed in claim 41 wherein a portion of said pressurized air flows past the fore end of said cylinder (14) and reverses and flows toward the aft end of said cylinder 14 and into the inlet apertures (70) of said cylinder (14), an axial slot formed adjacent to said apertures for leading said portion of pressurized air into the cylinder (14).

43. A surgical motor (51) as claimed in claim 42 wherein said cylinder includes a plurality of circumferential and axially spaced discharge cylindrical holes (72) and said discharge holes being cylindrically shaped.

44. A modular surgical motor (51) as claimed in claim 43 wherein the inlet apertures (70) are cylindrical in shape.

45. A surgical motor (51) as claimed in claim 44 wherein said discharge apertures (72) are prearranged in a given pattern of columns and rows, each row of apertures (72) do not overlap the next adjacent row of apertures, the straight edge (73) of vanes (24) as it travels over the columns of apertures (72) are arranged to provide a constant surface contact with the surface of said cylinder (14) during each revolution of travel creating uniform wear of said straight edge (73) enhancing the life of said vane motor (55).

46. A surgical motor (51) as claimed in claim 45 including a disc shaped first seal (22*a*) mounted in the seal housing (7) and wedged between the seal support washer rigidly supported in a fixed position in insert housing (2) and ball bearing (9), said ball bearing (9) having an inner race (9*a*), said seal (22*a*) extending from the seal support housing to said inner race (9*a*) and defining a minuscule gap for permitting a minuscule amount of air/oil mist to escape and causing the air/oil to flow toward the center of said spindle (4).

47. A surgical motor (51) as claimed in claim 46 including seal (22) shaped in the form of a disc mounted adjacent the spindle stub shaft (61) to prevent leakage of oil from said bearing (9), seal support washer (10) and seal retaining nut (23) mounted in said insert housing, seal (22) wedged between said seal support washer (10) and said seal retaining nut (23) and adjacent said stub shaft (61), said seal (22) being made from a thermal setting material and being made operable in situ by rotating said stub shaft (61) of said vane motor to generate sufficient friction and heat to cause said seal (22) to deform in the shape of the contour of the face of seal retaining nut (23) and become operable wherein the edge of said seal (22) deforms to define a minuscule gap between said seal (22) and stub shaft (61) to prevent oil from leaking while allowing air to leak and seal (22) being axially spaced from seal (22*a*).

48. A surgical motor (51) as claimed in claim 47 including a pair of diametrically opposed balls (12) made from elastomeric material whereby the vibrations of said vane motor are attenuated, said means for coupling include a drive pin (11) extending laterally from said input shaft (61) and fitted into a aperture formed therein, a coupling nut (5) attached to said input shaft (61) and having pockets contoured to support said balls (12) whereby the rotary motion from said spindle (4) is transferred to said output shaft (6) via the balls (12) for reducing vibration and noise.

* * * * *